United States Patent
Tepic

[19]

[11] Patent Number: 6,005,163
[45] Date of Patent: Dec. 21, 1999

[54] METHOD FOR CEMENTING AN IMPLANT INTO BONE

[75] Inventor: Slobodan Tepic, Davos, Switzerland

[73] Assignee: AO-Forschungsinstitut Davos, Switzerland

[21] Appl. No.: 08/925,789

[22] Filed: Sep. 9, 1997

Related U.S. Application Data

[63] Continuation of application No. 08/613,063, Mar. 8, 1996, abandoned.

[51] Int. Cl.$^6$ ........................................................ A61F 2/28
[52] U.S. Cl. .................................................................. 623/16
[58] Field of Search ................................. 623/16, 18, 20, 623/22, 23, 66; 606/76, 86

[56] References Cited

U.S. PATENT DOCUMENTS 4,280,233  7/1981  Raab ........................................ 623/18
4,281,420  8/1981  Raab ........................................ 623/18

*Primary Examiner*—David J. Isabella
*Attorney, Agent, or Firm*—Karen Lee Orzechowski; Alston & Bird, LLP

[57] ABSTRACT

In this method for cementing an implant into bone by means of an autopolymerising two-component bone cement the implant, in particular the stem of a hip prosthesis is preheated above room-temperature prior to its cementing into bone, preferably to at least 43° C.

By this method the stem-cement interface is warmer than the bone-cement interface and consequently a stiff cement shell will form first around the stem and the cement will shrink towards the stem and away from the bone. The resulting reduction of porosity at the stem-cement interface improves significantly the fatigue life of the system.

17 Claims, 6 Drawing Sheets

METHOD FOR CEMENTING AN IMPLANT INTO BONE

This application is a Continuation of U.S. patent application Ser. No. 08/613,063, filed Mar. 8, 1996 abandoned.

FIELD OF THE INVENTION

This invention relates to a method for cementing an implant into bone by means of an autopolymerising two-component bone cement.

BACKGROUND ART

It is standard practice to fix implants, in particular endo-joint implants into bone by means of an autopolymerising two-component bone cement prepared by mixing liquid methylmethacrylate (MMA) with polymethylmethacrylate (PMMA) in powder form.

The use of polymethylmethacrylate (PMMA) cement in total hip replacement has been extremely successful since its introduction by Charnley in 1960. However, many revisions are still required every year and a large majority of these are due to aseptic loosening (Stauffer et al 1982; Sutherland et al 1982; Fournasier et al 1976). In particular, it is the loosening of the femoral component which accounts for the majority of such cases (Poss et al 1970; Jasty et al 1991). Failure of the cement mantle is believed to initiate at the stem-cement interface (James et al 1993; Culleton et al 1993; Jasty et al 1991) which is significantly weaker than the bulk cement under static and fatigue loading (Raab et al 1981). Furthermore, a number of studies indicate that the stresses become significantly higher in the cement mantle once the stem-cement interface has become loose (Harrigan et Harris 1991; Crowninshield et Tolbert 1983; Freitag et Cannon 1977).

Both the static and fatigue strength of bone cement decrease with porosity (James et al 1992; Burke et al 1984; Saha et al 1984; DeWijn et al 1975; Greenwald et al 1977) and the stem-cement interface strength is similarly affected (Welsh et al 1971, James et al. 1993). Fatigue is the most credible mode of mechanical failure of the cement mantle (Harris et Davies 1988) and any measure to reduce the porosity of both the bulk cement and its interface to the prosthesis should be of clinical benefit.

Pores in the bulk cement result primarily from air bubbles which become entrapped during hand mixing of the powder and liquid components. It is also thought that monomer evaporation at the high temperatures of polymerisation due to its volatility may contribute to pore formation (Debrunner et al 1976). The bubbles act as stress risers of at least factor two (Timoshenko & Goodier 1934; Burke et al 1984; Freitag et al 1977; Carter et al 1982; Gates et al 1983) and it has been reported that failure in fatigue has occurred in test specimens almost exclusively through a pore (cited in James et al 1992). Reduction in porosity has been achieved using two techniques: centrifugation (Burke et al 1984) and mixing under vacuum (Schreurs et al 1988; Lidgren et al 1987). Other methods to decrease the porosity include pressurising cement (Saha et Pal 1984) and the use of improved hand mixing technique (Eyerer et Jin 1986).

The stem-cement interface strength can be improved by precoating of the stem with a thin layer of PMMA under optimal polymerisation conditions (Ahmed et al 1984). Under static testing of the precoated interfaces the bulk PMMA fractured preferentially to the stem-cement interface, thus implying an interface strength in excess of the bulk cement strength. Roughening the implant surface, both on the micro and macro scale, improves the interface strength, but it also increases stresses in the cement mantle (Stone et al 1989; Welsh et al 1971).

The bone-cement interface appears to be less critical in loosening and is believed to be due to biological factors rather than mechanical (Schmalzried et al 1992). There are a number of practised techniques which are used to ensure an optimal cement-bone interface (Krause et al 1982). These include thorough cleaning of the canal using pressurised water picks, and the pressurisation of cement into the cancellous bone interstices (Bourne et al 1984). This ensures maximum area for load transfer. However, Noble and Swarts (1983) have shown that a penetration of more than 5 mm is likely to cause thermal damage to the bone and from mechanical considerations more than 2.9 mm is possibly superfluous (Jansson 1993).

The heat of polymerisation of PMMA cement is considered to be an important factor in initial bone necrosis (Dipisa et al 1976). Lenhartz (1959) cites the threshold temperature of collagen denaturation (56° C.) as the criterion for bone necrosis. However, Moritz and Henriques (1947) present a time dependant threshold level for cell necrosis (e.g. a temperature of 50° C. for three minutes will kill bone cells). Toksvig-Larsen et al. (1991) measured a mean maximum temperature of 40° C. at the cement-bone interface using lavage and vacuum mixed cement. They found that cooling of the stem prior to implantation had no affect on the peak cement temperature and indeed this increases the setting time of the cement (De Waal Malefijt et al 1987) and compromises its mechanical properties.

Porosity at the stem-cement interface is caused by shrinkage of the cement. If the stem is implanted at room temperature the cement at the warmer bone-cement interface will polymerise first, creating a stiff shell towards which cement will shrink. Thus, the cement shrinks away from the stem, creating pores at the areas of least adhesion.

SUMMARY OF THE INVENTION

The invention as claimed aims at solving the above described problems by providing a method for cementing an implant into bone by means of an autopolymerising two-component bone cement, whereby the implant is preheated above room-temperature prior to its cementing into bone.

If the stem-cement interface is warmer than the bone-cement interface a stiff cement shell will form first around the stem and the cement will shrink towards the stem and away from the bone. Reduction of porosity at the stem-cement interface improves significantly the fatigue life of the system.

Instead of heating the stem the bone could be cooled alternatively. However, cooling of the bone leads to retarded polymerisation and weaker cement (Tepic 1995). Therefore moderate heating of the stem prior to implantation is the optimal way to reverse the direction of polymerisation, thereby dramatically reducing the porosity of the bone cement at the stem-cement interface.

The various features of novelty which characterize the invention are pointed out with particularity in the claims annexed to and forming part of this disclosure. For the better understanding of the invention, its operating advantages and specific objects attained by its use, reference should be had to the accompanying drawings, examples and descriptive matter in which are illustrated and described preferred embodiments of the invention.

DETAILED DESCRIPTION OF THE INVENTION

Figure 1:
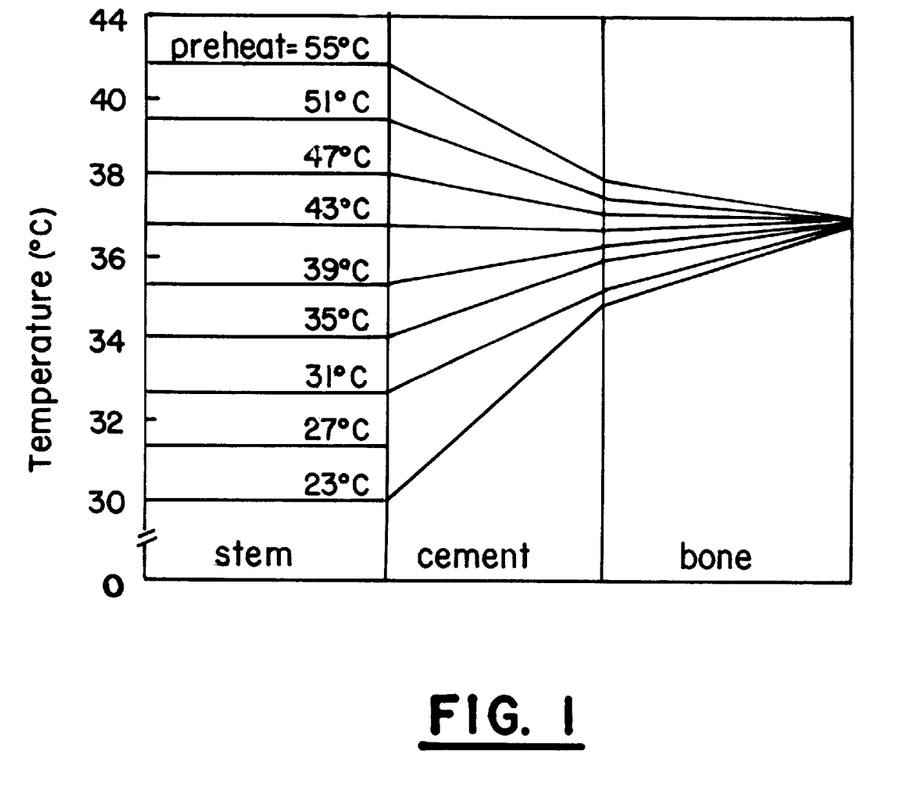
FIG. 1 shows the temperature distribution in the stem-cement-bone system just prior to polymerisation.
Figure 2:
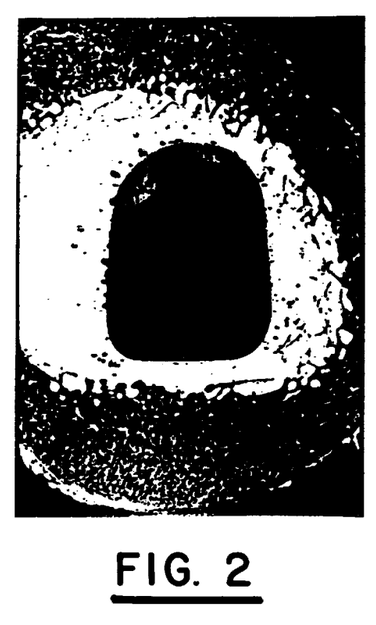
FIG. 2 shows a cross section at the distal third of the stem.
Figure 3:
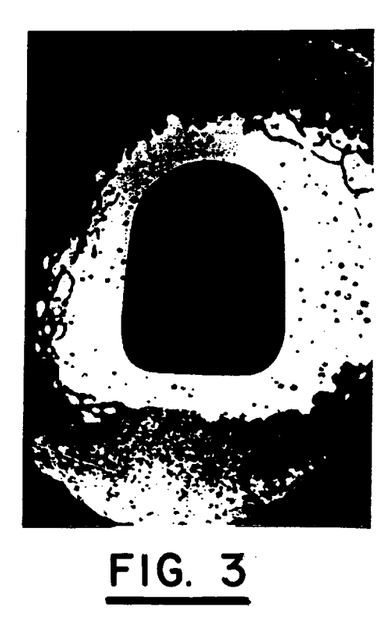
FIG. 3 shows another cross section at the distal third of the stem.
Figure 4:
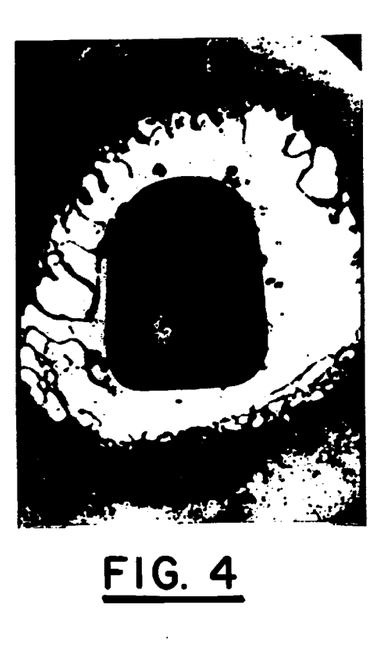
FIG. 4 shows still another cross section at the distal third of the stem.
Figure 5:
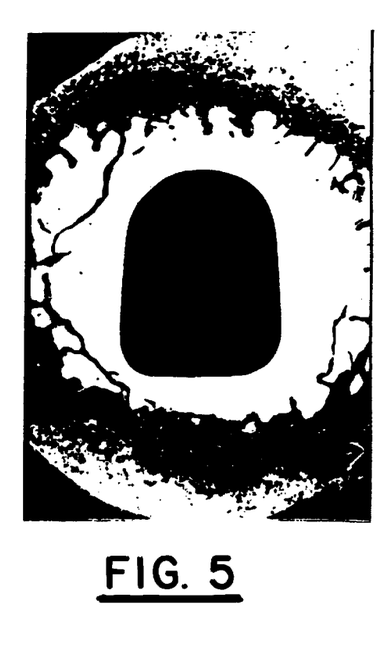
FIG. 5 shows still another cross section at the distal third of the stem.
Figure 6:
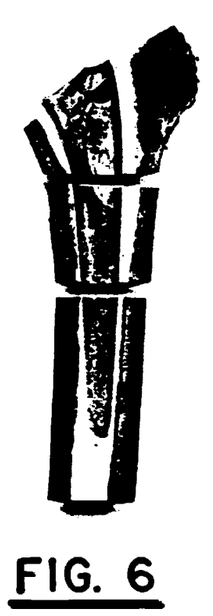
FIG. 6 shows a longitudinal section of the stem-cement interface.
Figure 7:
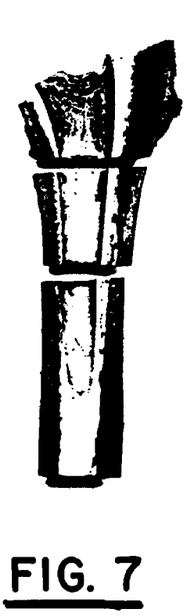
FIG. 7 shows another longitudinal section of the stem-cement interface.
Figure 8:
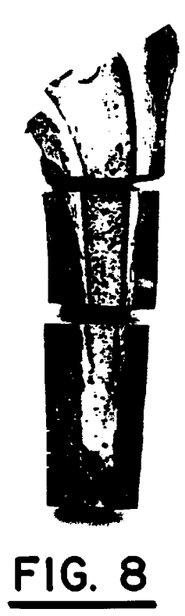
FIG. 8 shows still another longitudinal section of the stem-cement interface.
Figure 9:
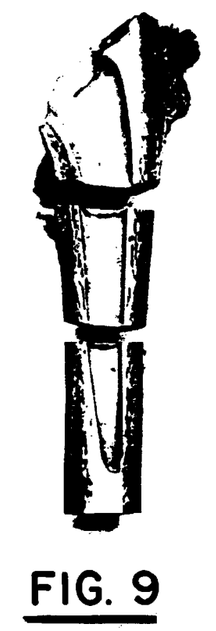
FIG. 9 shows still another longitudinal section of the stem-cement interface.
Figure 10:
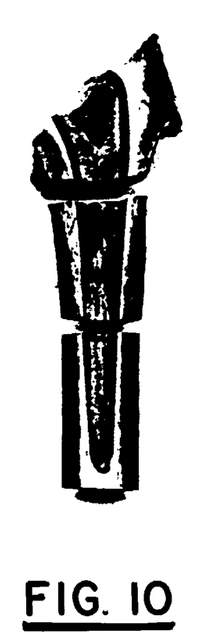
FIG. 10 shows still another longitudinal section of the stem-cement interface.
Figure 11:
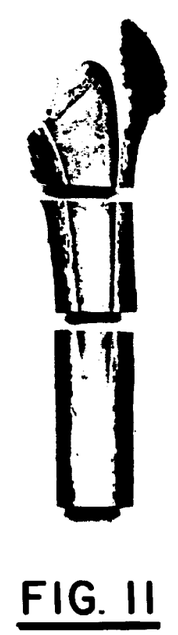
FIG. 11 shows still another longitudinal section of the stem-cement interface.
Figure 12:
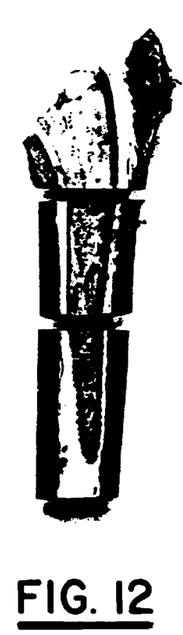
FIG. 12 shows still another longitudinal section of the stem-cement interface.
Figure 13:
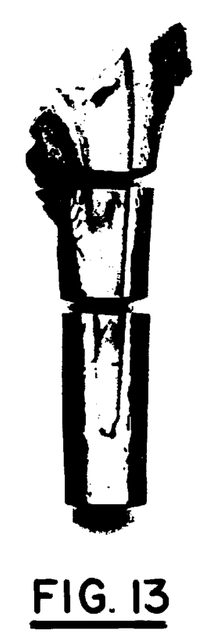
FIG. 13 shows still another longitudinal section of the stem-cement interface.

The formation of voids due to shrinkage of the cement is dependent on the difference in temperatures between the bone-cement interface and the stem-cement interface at the onset of polymerisation. The onset of polymerisation of the cement is influenced by many factors, most strongly by the room temperature. Typically the onset of polymerisation of the cement occurs approximately three minutes after stem insertion. During this time, heat is redistributed throughout the stem-cement-bone system and the temperature of each cement interface will change. An iterative computer model was used to determine the temperature distribution in the system over time. The theoretical temperature distribution in the stem-cement-bone system just prior to polymerisation is shown in FIG. 1 for varying stem implantation temperatures. For a standard implantation, using a stem at a room temperature of 23° C. and maintaining the outer surface of the bone at 37° C., the bone-cement interface is at least 5° C. hotter than the stem-cement interface at 3 minutes. For a stem implanted at 43° C. or higher, the stem-cement interface is warmer than the bone-cement interface at the onset of polymerisation.

In an experimental study, the stems were preheated to 44° C., which is just above the minimum theoretical temperature required for shrinkage onto the stem. Two commonly used cements were tested: Palacos R with Gentamicin antibiotic (Kulzer) and Sulfix 60 (Sulzer). Sulfix 60 is a low viscosity cement and is thus recommended for vacuum mixing to allow better escape of bubbles. Hand mixed cement was prepared following standard clinical technique. Vacuum mixed cement was prepared using the Optivac system (Mitab) in which the monomer and powder are mixed with a plunger in an evacuated syringe. This method of mixing is clinically well accepted. It yields very low porosity cement and thus the only bubbles which form (and are visible) are due to shrinkage effects during polymerisation.

The stainless steel MS30 femoral component (Protek), which has a fine blasted surface finish, was implanted in human cadaveric femora. The bones were reamed and four holes were drilled in the cortex for thermistor insertion, equally spaced along the stem length. The bones were then heated in a 37° C. water bath. A distal cement plug was inserted and cement was introduced into the bone from distal to proximal using a cement gun and delivery nozzle. The stem was implanted into the more viscous Palacos cement at approximately 3.5 minutes after the start of mixing of monomer and powder leaving a further 3 minutes before the onset of polymerisation at 6.5 minutes. Implantation into the less viscous Sulfix 60 was carried out at 4 minutes, again allowing 3 minutes before the onset of polymerisation. The bones were kept submerged in the water bath during implantation and thereafter for three days, to ensure sufficient polymerisation. The bone cortex temperatures were recorded for up to twelve minutes after stem implantation.

The implanted femora were sectioned transversely and longitudinally for evaluation. The bone was stained with Van Giemson to allow better differentiation between the trabeculae and the cement. The stem sections were removed from the cement and the interface was wiped thoroughly with permanent ink in order to stain any pores. The cement surface was then photographed by a video camera linked to an image analysis system (Kontron) and the pore area was measured within six 7 mm×14 mm areas spaced evenly along the length of the stem-cement interface. Electron micrographs were also made of the cement surfaces for visual inspection.

FIGS. 2–5 show cross sections at the distal third of the stem. Implantation of the room temperature stems into both hand mixed and vacuum mixed cement (FIG. 2 and FIG. 4) shows pores to be concentrated around the stem. The vacuum mixed cement has a very low bulk porosity indicating that the pores around the stem implanted at room temperature formed due to the shrinkage effects of polymerisation. In contrast, in samples implanted with a 44° C. stem (FIG. 3 and FIG. 5) there are no pores evident at the stem-cement interface. Close inspection of the trabeculae reveals that in these cases the cement has separated from the trabeculae towards the stem.

Figure 14:
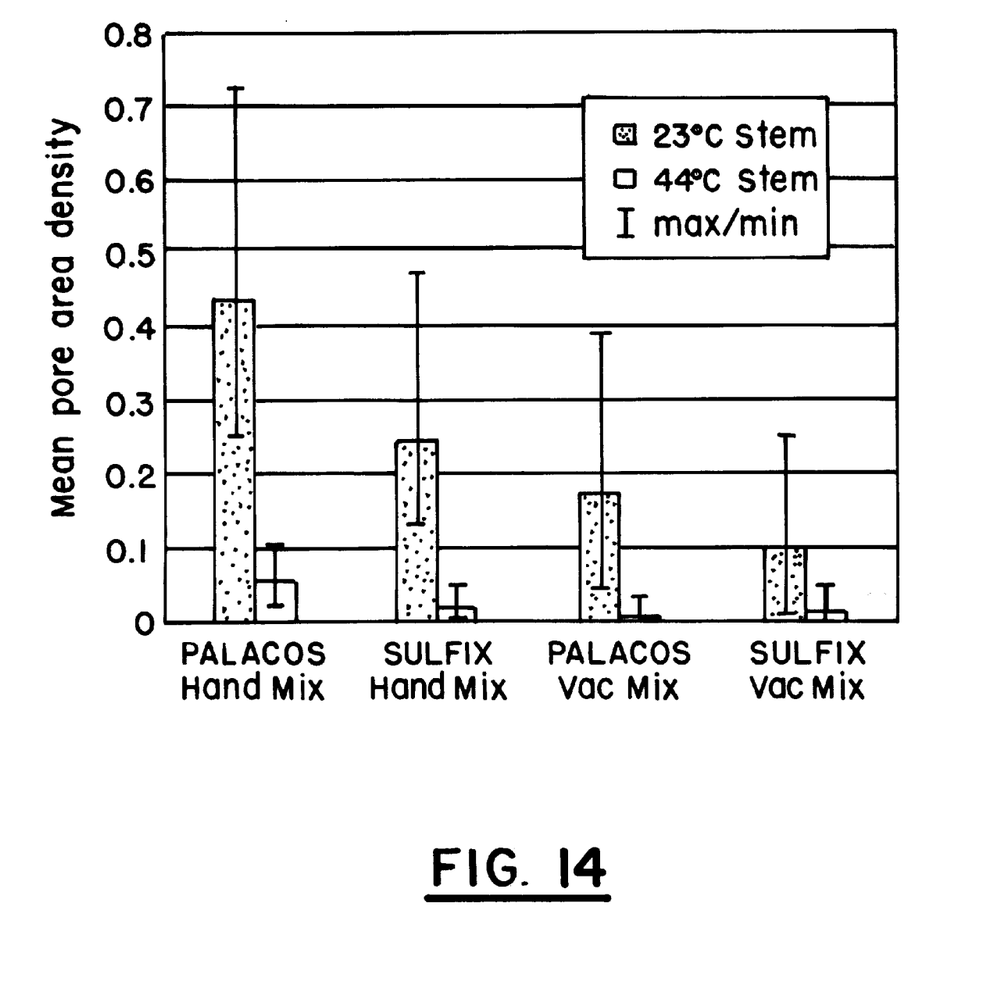
FIG. 14 shows a graph with the mean porosities of the six areas measured on one side of each implantation specimen.
Figure 15:
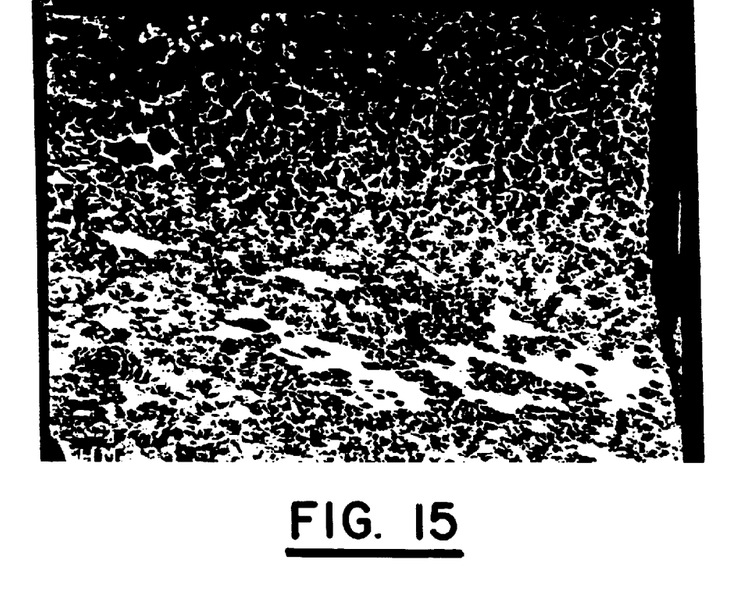
FIG. 15 shows a representative area in an electronmicrograph.
Figure 16:
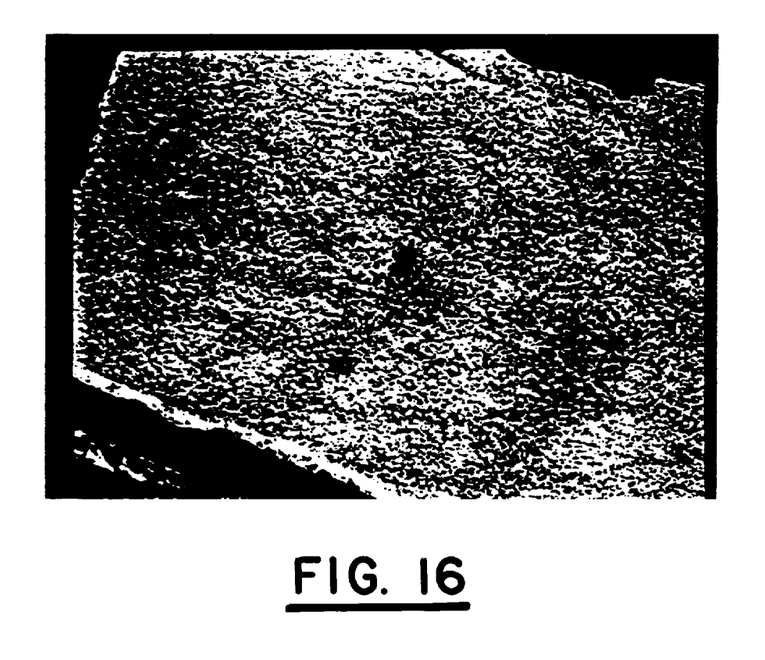
FIG. 16 shows another representative area in an electronmicrograph.

Longitudinal sections of the stem-cement interface are shown in FIGS. 6–13. Preheated stems were implanted in samples shown in FIGS. 7,9,11 and 13. In some samples there are large voids in the cement in the proximal mantle due to imperfect insertion. These are not due to shrinkage effects. These results are described quantitatively in FIG. 14. This graph shows the mean porosities of the six areas measured on one side of each implantation specimen. Vacuum mixing results in a less porous stem-cement interface than hand mixing and heating of the stem results in a less porous interface for both hand mixed and vacuum mixed cements. Both cement types when hand mixed and implanted with a cold stem have a high density of small pores. This is consistent with the observations of James et al (1993). A representative area of this surface is shown in an electronmicrograph (FIG. 15), along with a sample using vacuum mixed cement and a pre-heated stem, which has no pores (FIG. 16).

Figure 17:
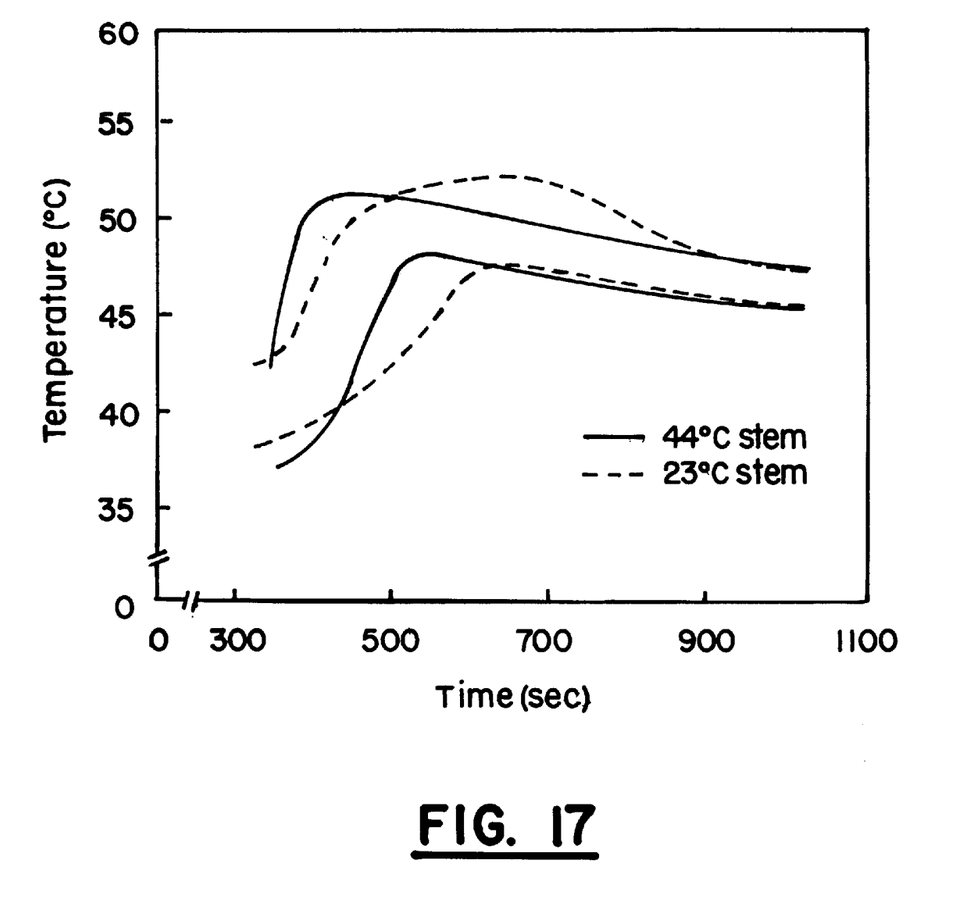
FIG. 17 shows a graph with temperatures measured in the bone cortex during cement polymerisation.

FIG. 17 shows the range of temperatures measured in the cortex during the implantation experiments. Implantation of the preheated stem (44° C. compared with 23° C.) leads to a more rapid polymerisation reaction. However, the peak temperatures measured in the cortex were similar for all cases, with a maximum difference of 2.2° C.

The peak temperatures are given in Table 1.

TABLE 1

|  | 44° C. stem | 23° C. stem |
| --- | --- | --- |
| Palacos R, hand mixed | 49.7 | 48.9 |
| Palacos R, vacuum mixed | 50.9 | 48.7 |
| Sulfix 60, hand mixed | 51.0 | 51.9 |
| Sulfix 60, vacuum mixed | 50.9 | 51.1 |
| Mean | 50.6 | 50.2 |

Discussion of the Experimental Results

Preheating of the stem to a minimum temperature required to initiate polymerisation at the stem dramatically reduces the pore area density of the cement at the stem-cement interface.

This interface is critical in fatigue failure of the cement mantle and reduction of porosity should prolong the life of the arthroplasty.

The temperature measurements taken during the in vitro implantation experiments show very little difference in the bone-cement interface temperature and bone peak temperature for the two different stem implantation temperatures. In neither case is cell damage expected, according to Moritz and Henriques (1947). Much higher temperatures (70° C.) may be withstood before the regenerative capacity of the bone tissue is permanently damaged (Lundskag 1983).

The MMA monomer increases in density from 0.943 kg/m$^3$ to 1.28 kg/m$^3$ on polymerisation and thus shrinks roughly 35%. However, because only 30% MMA monomer is added to the PMMA powder the overall shrinkage of the bone cement is roughly 5% (Haas et al 1975). There will also be thermal volume changes due to the heat of polymerisation. Ahmed et al (1982) measured the thermal expansion of hand mixed bone cement to be 0.47×10$^{-4}$ which would give a volume change of around 0.2% for a 40° C. temperature change (i.e. from 77° C.–37° C. for cooling of a hot cement mantle to body temperature). Air bubbles in the cement will also expand thermally but because the cement is contained between the implant and the bone they will cause little volume change due to the compressibility of the gas. Thus, it appears that porosity is caused primarily by bulk shrinkage.

As the cement shrinks residual stresses will be induced in the cement mantle. However, these stresses do not appear to be critical and are likely to decrease over time due to relaxation. In any case there is little difference in such residual stresses whether the stem is heated or not (because the cement shrinkage is a constant).

The cement shrinkage onto the preheated stem implies that the cement will pull away from the bone interface towards the stem. Due to lack of bonding between bone and cement, cement shrinkage results in a uniform gap and no stress raising pores are created. Shrinkage displacements are small compared to the size of the macro interlock in the bone trabeculae, so that load bearing capacity at this interface is minimally compromised.

Conclusions

If a stem of room temperature is implanted into the bone at approximately body temperature, bone cement will polymerise from the bone towards the stem. This will induce pores to form in the cement mantle near and at the stem-cement interface. These pores are significant stress risers and lead to an early fatigue failure of the cement.

In Vitro implantation into human cadaveric femora, using both normal and low viscosity cements, mixed by hand and under vacuum, showed practical elimination of shrinkage induced pores at the stem-cement interface for the preheated prosthesis.

On average the peak temperature at the middle of the cortex was 50.6° C. for the preheated stem and 50.1° C. for the room temperature stem. The maximum difference recorded was 2.2° C.

This simple procedure significantly improves the long term performance of cemented total hip replacement or other cemented implant. Other implantations whose performance will benefit from the method according to the invention are knee replacements, acetabular replacements and dental implantations, all of which are subjected to high fatigue loads. In such cases the thermal characteristics, which depend upon geometry, materials and initial temperatures of each component may be considerably different to the situation described for the hip prosthesis. Thus the preheat temperature requirement may be higher where there is less thermal resistance and thus greater heat flow. The bone temperature could be less than 37° C. if the blood supply has been disrupted or the bone washed with water at a lower temperature (e.g. room temperature). Thus any implant will usually require preheating at least above room temperature, but preferably above body temperature, most preferably to 43° C. or 44° C. Purposefully the said implant should be preheated to a temperature that is at least 6° C. higher than the bone into which it is to be implanted.

Preheating of the implant can be achieved in different ways. The implant can simply be heated in a waterbath or an oven or alternatively the implant can be heated by an additional heating device which is either permanently connected or connectable to the implant. It is necessary that the additional heating device is sterilisable and desirable that it heats up quickly and maintains its temperature until the implant is removed therefrom. Such an additional heating device can utilise electrical or chemical energy. An electrical device requires a heating element which can be powered either by a local battery pack or by an external supply and linked with a thermostat device. Alternatively, the battery itself can be short-circuited by a thermostat device and used as a heating element (by dissipation through internal resistance). An electrical voltage can be applied across a conductive implant, whereby the implant act as a resistor and consequently heats up.

Chemical means of heating the implant are utilising a set amount of heat produced by an exothermic reaction or by utilising the heat produced at a constant temperature during the phase transition of a chemical, i.e. either SOLID←→LIQUID, ←→GAS or SOLID←→GAS. In this case the temperature of the phase transition would be matched to the required preheat temperature. In a preferred embodiment the solid/liquid phase transition can be utilised, whereby the liquid is in a supercooled state at room temperature (i.e. remains liquid below its melting point, which is the preheat temperature). When sufficient initiation energy and a nucleation site are supplied, the chemical solidifies at the melting (preheat) temperature. The initiation energy can easily be supplied by releasing a spring, which can also act as a nucleation site. Such chemicals are hydrated sodium acetate ($C_2H_3NaO_2.3H_2O$) with the melting point of 58° C. or sodium thiosulfate pentahydrate ($NaS_2O_3.5H_2O$) with a melting point range of 40–45° C. Sufficient quantities of these compounds can warm up and maintain the implant at the transition temperature for many minutes. A solid/liquid phase transition is particularly desirable as the liquid may be sealed in a plastic bag which is wrapped around the implant and will conform to its profile, thus ensuring good thermal contact.

In a preferred embodiment the implant is located in a package which upon opening of the package or minimal manipulation, activates a heating device which effects the preheating of the implant. An electrical heating element can be activated by completing the circuit. A chemical reaction can be initiated by breaking a phial containing one of the reactants. The phase transition can be initiated mechanically, as described above.

If the bone cement is mixed conventionally, i.e. without application of vacuum its temperature should preferably be held between 18 and 25° C. prior to cementing of the implant. If, however, the autopolymerising cement is partial-vacuum-mixed it has proved beneficial to cool the cement to 5–10° C. prior to cementing the implant.

While the foregoing description and drawings represent the preferred embodiments of the present invention, it will be obvious for those skilled in the art that various changes and modifications may be made therein without departing from the true spirit and scope of the present invention.

I claim:

1. A method for cementing an implant into bone by placing an autopolymerising cement on or in the bone to be treated and placing the implant in contact with said cement so that a layer of said cement remains between the implant surface and the bone, said cement comprising at least a monomer and a polymerization initiator, wherein polymerization of said cement is caused to start first at the implant/cement interface and wherein the surface of said implant is caused to be hotter that the surface of said bone at the onset of polymerization.

2. A method for cementing an implant into bone by placing an autopolymerising cement on or in the bone to be treated and placing the implant in contact with said cement so that a layer of said cement remains between the implant surface and the bone, said cement comprising at least a monomer and a polymerization initiator, wherein polymerization of said cement is caused to start first at the implant/cement interface and wherein a layer of said initiator is applied to the surface of the implant prior to polymerization.

3. The method according to claim 1, wherein said implant is preheated ex vivo prior to cementing said implant into said bone.

4. The method according to claim 3, wherein said implant is preheated above a room temperature of 23° C.

5. The method according to claim 3, wherein said implant is preheated to at least 20° C.

6. The method according to claim 3, wherein said implant is preheated above normal body temperature.

7. The method according to claim 3, wherein said implant is preheated to at least 43° C.

8. The method according to claim 3, wherein said implant is preheated to at least 44° C.

9. The method according to claim 3, wherein said implant is preheated to a temperature that is at least 6° C. higher than the bone temperature of 37° C.

10. The method according to claim 1, wherein said bone is precooled prior to cementing said implant therein.

11. The method according to claim 1, wherein said autopolymerizing cement is partial-vacuum-mixed and the implant is preheated.

12. The method according to claim 11, wherein said cement is cooled to 5–10° C. prior to cementing said implant.

13. The method according to claim 1, wherein said cement is held at a temperature between 18 and 25° C. prior to cementing said implant.

14. The method according to claim 1, wherein said implant is placed in a package and heated by means of exothermically reacting chemical compounds.

15. The method according to claim 14, wherein said exothermically reacting chemical compounds comprise hydrated sodium acetate ($C_2H_3NaO_2.3H_2O$).

16. The method according to claim 14, wherein said exothermically reacting chemical compounds comprise sodium thiosulfate pentahydrate ($NaS_2O_3.5H_2O$).

17. The method according to claim 1, wherein said implant is preheated to at least 50° C.

* * * * *